United States Patent
Guo et al.

(10) Patent No.: US 11,606,896 B2
(45) Date of Patent: Mar. 21, 2023

(54) PREDICTING SOIL ORGANIC CARBON CONTENT

(71) Applicant: X Development LLC, Mountain View, CA (US)

(72) Inventors: Cheng-en Guo, Santa Clara, CA (US); Jie Yang, Sunnyvale, CA (US); Zhiqiang Yuan, San Jose, CA (US); Elliott Grant, Woodside, CA (US)

(73) Assignee: MINERAL EARTH SCIENCES LLC, Mountain View, CA (US)

( * ) Notice: Subject to any disclaimer, the term of this patent is extended or adjusted under 35 U.S.C. 154(b) by 109 days.

(21) Appl. No.: 17/147,048

(22) Filed: Jan. 12, 2021

(65) Prior Publication Data

US 2022/0217894 A1    Jul. 14, 2022

(51) Int. Cl.
*A01B 79/00*      (2006.01)
*G01N 33/24*      (2006.01)
*G06T 7/00*       (2017.01)
*G06V 20/10*      (2022.01)

(52) U.S. Cl.
CPC .......... *A01B 79/005* (2013.01); *G01N 33/24* (2013.01); *G06T 7/0004* (2013.01); *G06V 20/188* (2022.01); *G06T 2207/30188* (2013.01)

(58) Field of Classification Search
CPC .. A61B 79/005; G06V 20/188; G06T 7/0004; G06T 2207/30188
See application file for complete search history.

(56) References Cited

PUBLICATIONS

Roy, Swapan Kumar, Sakae Shibusawa, and Tsuyoshi Okayama. "Textural analysis of soil images to quantify and characterize the spatial variation of soil properties using a real-time soil sensor." Precision Agriculture 7.6 (2006): 419-436. (Year: 2006).*

Yang, Lin, et al. "Predicting soil organic carbon content in croplands using crop rotation and Fourier transform decomposed variables." Geoderma 340 (2019): 289-302. (Year: 2019).*

Cunha, Renato LF, Bruno Silva, and Marco AS Netto. "A scalable machine learning system for pre-season agriculture yield forecast." 2018 IEEE 14th International Conference on e-Science (e-Science). IEEE, 2018. (Year: 2018).*

Yang, Jiechao, et al. "Combination of Convolutional Neural Networks and Recurrent Neural Networks for predicting soil properties using Vis-NIR spectroscopy." Geoderma 380 (2020): 114616. (Year: 2020).*

(Continued)

*Primary Examiner* — Vu Le
*Assistant Examiner* — Tracy Mangialaschi
(74) *Attorney, Agent, or Firm* — Gray Ice Higdon

(57) ABSTRACT

Implementations are described herein for predicting soil organic carbon ("SOC") content for agricultural fields detected in digital imagery. In various implementations, one or more digital images depicting portion(s) of one or more agricultural fields may be processed. The one or more digital images may have been acquired by a vision sensor carried through the field(s) by a ground-based vehicle. Based on the processing, one or more agricultural inferences indicating agricultural practices or conditions predicted to affect SOC content may be determined. Based on the agricultural inferences, one or more predicted SOC measurements for the field(s) may be determined.

18 Claims, 5 Drawing Sheets

(56) References Cited

PUBLICATIONS

O'Grady, M. J., D. Langton, and G. M. P. O'Hare. "Edge computing: A tractable model for smart agriculture?." Artificial Intelligence in Agriculture 3 (2019): 42-51. (Year: 2019).*

European Patent Office; International Search Report and Written Opinion issued in Application No. PCT/US2022/011938; 11 pages; dated Apr. 22, 2022.

Yang J. et al.; Combination of Convolutional Neural Networks and Recurrent Neural Networks for Prediction Soil Properties Using Vis-NIR Spectroscopy; Geoderma, Elsevier; 16 pages; dated Aug. 11, 2020.

Roy S.K. et al.; Textural Analysis of Soil Images to Quantify and Characterize the Spatial Variation of Soil Properties using a Real-Time Soil Sensor; Precision Agriculture; Kluwer Academic Publishers; vol. 7 No. 6; Springer; pp. 419-436; dated Oct. 20, 2006.

Oliveira, I. et al.; A Scalable Machine Learning System for Pre-Season Agriculture Yield Forecast; 2018 IEEE 14th International Conference on e-Science; pp. 423-430; dated Apr. 29, 2018.

Wang et al., "No tillage increases soil organic carbon storage and decreases carbon dioxide emission in the crop residue-returned farming system" Journal of Environment Management (2020) Elsevier Ltd.

King et al. "Crop rotations for increased soil carbon: perenniality as a guiding principle" Ecological Applications, 28(1), 2018, pp. 249-261. Ecological Society of America.

Yang et al., "Improving prediction of soil organic carbon content in croplands using phenological parameters extracted from NDVI time series data" Soil & Tillage Research. 2019. Elsevier B.V.

Zhu et al., "A Novel Method for Soil Organic Matter Determination by Using an Artificial Olfactory System" Sensors 2019, 19, 3417. doi:10.3390/s19153417.

Taghizadeh-Mehrjardi et al., "Improving the Spatial Prediction of Soil Organic Carbon Content in Two Contrasting Climatic Regions by Stacking Machine Learning Models and Rescanning Covariate Space" Remote Sens. Dec. 2020, 1095: doi:10.3390/rs12071095.

Bangelesa et al., "Predicting Soil Organic Carbon Content Using Hyperspectral Remote Sensing in a Degraded Mountain Landscape in Lesotho" Hindawi. Applied and Environmental Soil Science vol. 2020, Article ID 2158573, 11 pages: https://doe.org/10.1155/2020/2158573.

Gehl et al., "Emerging technologies for in situ measurement of soil carbon" Springer Science + Business Media B.V. 2006. DOI: 10.1007/s10584-006-9150-2.

Vaudour et al., "The Impact of Acquisition Date on the Prediction Performance of Topsoil Organic Carbon from Sentinel-2 for Croplands" Remote Sens. Nov. 2019, 2143: doi:10.3390/rs11182143.

\* cited by examiner

PREDICTING SOIL ORGANIC CARBON CONTENT

BACKGROUND

Organic content such as carbon gives soil structure and retains water and nutrients needed for plants, fungi, and soil bacteria to thrive. The detection and management of the organic carbon content of soil is important to many farming and agricultural practices. Many factors affect the organic carbon content of soil in a particular environment, including, but not limited to: climate and weather-related factors; presence of animals, plants, fungi, and bacteria; and human-influenced factors (captured in what will be referred to herein as "operational data"), including application of pesticides, application of fertilizers, crop rotation, applied irrigation, soil management, crop choice, and disease management, to name a few.

SUMMARY

While efforts have been made to predict soil organic carbon (SOC) content based on high-elevation imagery such as satellite data, these efforts have had limited success. High-elevation digital imagery presents various challenges, such as the fact that 30-60% of such images tend to be covered by clouds, shadows, haze and/or snow. Moreover, the usefulness of these high-elevation digital images is limited by factors such as observation resolutions and/or the frequency at which they are acquired.

Accordingly, implementations are described herein for predicting SOC content based on a variety of different factors, particularly factors other than high-elevation digital imagery (although high-elevation digital imagery can still be used in conjunction with various data points described herein). For example, implementations described herein may leverage local observational data, which is becoming increasingly available in the agriculture domain as more agricultural robots are deployed into the fields to perform various agricultural tasks. For example, various types of local sensor data related to soil quality, aeration, tillage, crop rotation, etc., may be captured by a variety of different nodes deployed at or near rural/remote field(s) in which crops are grown. These nodes may include robots (land-based or aerial), data processing devices operated/carried by agricultural personnel at or near the edge, and/or sensors deployed on farm equipment, to name a few.

Some implementations described herein relate to using machine learning to predict SOC based on, among other things, local sensor data that is indicative of (and hence, can be used to predict) how cropland is managed by humans. In various implementations, one or more machine learning models, such as a convolutional neural network model (CNN), a recurrent neural network (RNN), or other deep learning model, may be trained to generate output that is indicative of predicted soil organic content for a particular geographic area, such as a field or group of fields. Inputs to such a model may include various combinations of inferred operational data points that are indicative of human management of cropland, as well as other observational data points such as climate data, etc.

In some implementations, machine learning models configured with selected aspects of the present disclosure may be used to predict a future measure of SOC content for a geographic region at a particular future time or during a particular future time interval using hypothetical or altered operational and/or observational data values. These hypothetical or altered operational and/or observational data values may be obtained from user input and/or scraped from one or more additional data resources, such as the web. For example, a farmer can provide a proposed tillage practice schedule for an upcoming growing season. The machine learning model may be used to process the various ground truth and predicted values, the altered tillage practices, and one or more publicly available climate change or weather pattern models to determine a likely SOC for the end of the upcoming growing season. The farmer may then be able to adjust various parameters to see how SOC content would be impacted.

In various implementations, a method may be implemented using one or more processors and may include: obtaining a plurality of digital images captured by one or more vision sensors carried throughout a field by one or more ground-based farm vehicles over a time period; processing the plurality of digital images to infer: one or more tillage practices implemented in the field over the time period, and a rotation of crops planted in the field over the time period; and based on the inferred one or more tillage practices and the inferred rotation of crops, predicting a measure of soil organic carbon (SOC) associated with the field.

In various implementations, the method may include obtaining a slope map of the field based on data generated by one or more sensors carried throughout the field by one or more of the ground-based farm vehicles, wherein the predicted measure of SOC is further predicted based on the slope map. In various implementations, the processing includes processing the plurality of images to predict a crop yield of the field during a crop cycle within the time period, wherein the measure of SOC is further predicted based on the predicted crop yield. In various implementations, the crop yield is further predicted based on local climate data or a temporal sequence of high-elevation digital images captured by a satellite.

In various implementations, the method may include operating a ground-based robot to carry one or more of the vision sensors through the field. In various implementations, at least some of the plurality of images are obtained from an edge-computing node that is mounted on a boom of a farm vehicle. In various implementations, the plurality of digital images are processed using one or more convolutional machine learning models, and wherein the measure of SOC is predicted using one or more other machine learning models.

In various implementations, the plurality of digital images are processed, and the measure of SOC is predicted, using a single time-series machine learning model. In various implementations, processing the plurality of digital images comprises processing the plurality of digital images to infer one or more cover crops planted in the field over the time period, and wherein predicting the measure of SOC associated with the field is performed further based on the inferred one or more cover crops.

In various implementations, the method may include: receiving indications of one or more tillage practices and rotations of crops likely to be implemented in the field during a future time period; and predicting a future measure of SOC associated with the field.

In a related aspect, a method may include obtaining a plurality of digital images captured by one or more vision sensors carried throughout a field by one or more ground-based farm vehicles over a time period; obtaining ground truth data indicative of a plurality of ground truth measures of SOC during the time period; iteratively applying digital images of the plurality of digital images as inputs across a time-series machine learning model to generate one or more outputs; based on the one or more outputs, determining a plurality of predicted measures of SOC; comparing the plurality of predicted measures of SOC to the corresponding ground truth measures of SOC; and training the time-series machine learning model based on the comparing.

In addition, some implementations include one or more processors (e.g., central processing unit(s) (CPU(s)), graphics processing unit(s) (GPU(s)), and/or tensor processing unit(s) (TPU(s)) of one or more computing devices, where the one or more processors are operable to execute instructions stored in associated memory, and where the instructions are configured to cause performance of any of the aforementioned methods. Some implementations also include one or more non-transitory computer readable storage media storing computer instructions executable by one or more processors to perform any of the aforementioned methods. Yet other implementations include agricultural vehicles, such as robots or tractors, that are equipped with edge processor(s) configured to carry out selected aspects of the present disclosure.

It should be appreciated that all combinations of the foregoing concepts and additional concepts described in greater detail herein are contemplated as being part of the subject matter disclosed herein. For example, all combinations of claimed subject matter appearing at the end of this disclosure are contemplated as being part of the subject matter disclosed herein.

DETAILED DESCRIPTION

Figure 1:
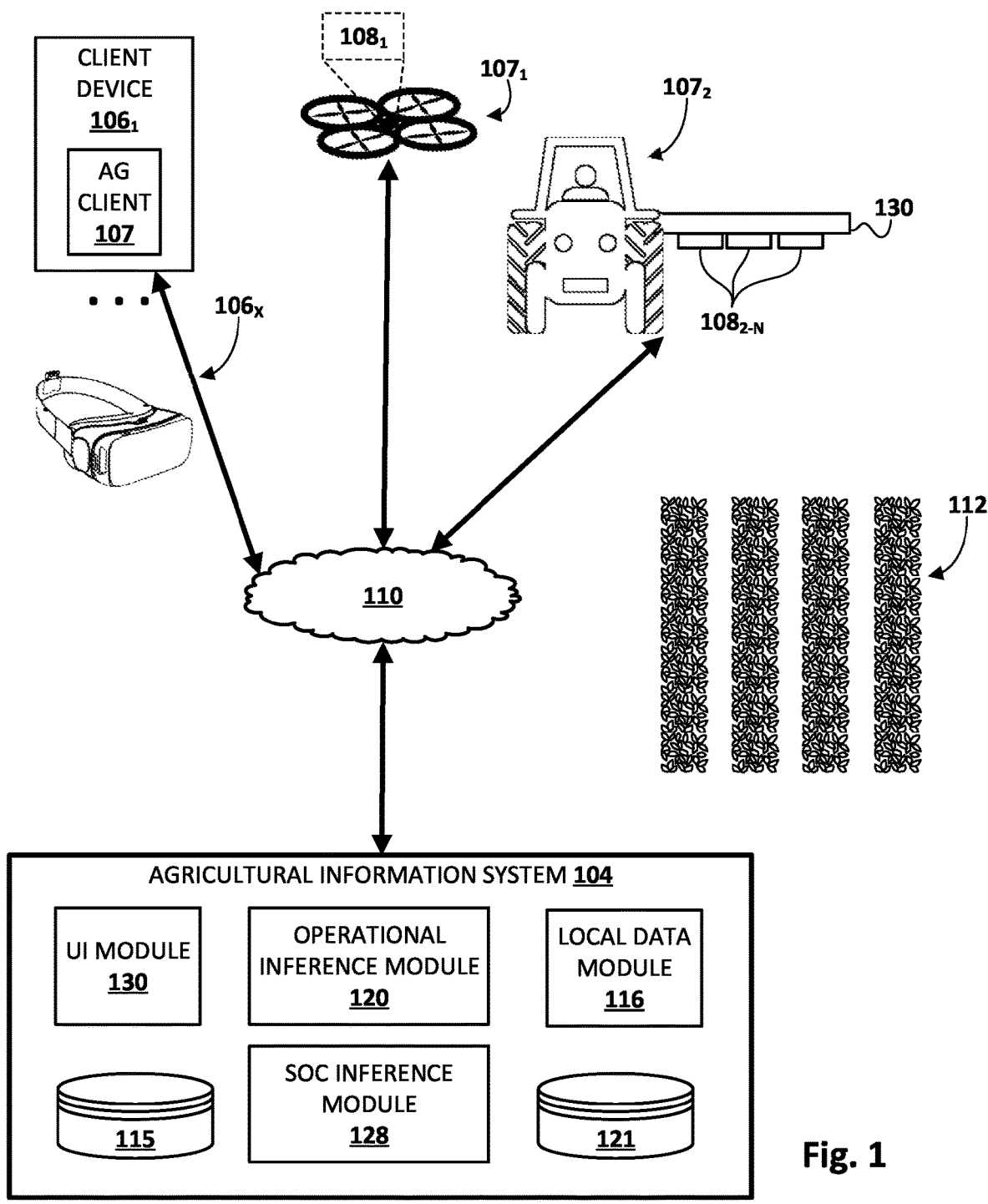
FIG. 1 schematically illustrates an example environment in which selected aspects of the present disclosure may be implemented.

FIG. 1 schematically illustrates an environment in which one or more selected aspects of the present disclosure may be implemented, in accordance with various implementations. The example environment includes an agricultural information system 104, one or more client devices $106_{1-X}$, and human-controlled and/or autonomous farm vehicles $107_{1-2}$ that can be operated to carry any number of sensors, such as vision sensors $108_{1-N}$, through one or more fields 112. While vision sensors $108_{1-N}$ are mounted to a boom 130 such that they would be carried over top of many crops, this is not meant to be limiting, and vision sensors 108 may be mounted on vehicles in other manners that provide other perspectives of crops, such as side views. The various components depicted in FIG. 1 may be in network communication with each other via one or more networks 110, such as one or more wide area networks ("WANs") such as the Internet, and/or via one or more local area networks ("LANs", e.g., Wi-Fi, Ethernet, various mesh networks) and/or personal area networks ("PANs", e.g., Bluetooth). Field(s) 112 may be used to grow various types of crops using various agricultural practices that may affect soil organic carbon ("SOC") content.

An individual (which in the current context may also be referred to as a "user") may operate a client device 106 to interact with other components depicted in FIG. 1. Each client device 106 may be, for example, a desktop computing device, a laptop computing device, a tablet computing device, a mobile phone computing device, a computing device of a vehicle of the participant (e.g., an in-vehicle communications system, an in-vehicle entertainment system, an in-vehicle navigation system), a standalone interactive speaker (with or without a display), or a wearable apparatus that includes a computing device, such as a head-mounted display ("HMD") that provides an AR or VR immersive computing experience, a "smart" watch, and so forth. Additional and/or alternative client devices may be provided.

Each of client devices 106 and/or agricultural information system 104 may include one or more memories for storage of data and software applications, one or more processors for accessing data and executing applications, and other components that facilitate communication over a network. In various implementations, some vision sensors 108, such as vision sensor $108_1$ associated with aerial drone $107_1$ and/or vision sensors $108_{2-N}$ mounted to a boom 130 of tractor $107_2$, may be integrated into a computing node (which may or may not be modular and/or removable from the vehicle 107 that carries it) that also includes logic such as processor(s), application-specific integrated circuits (ASICs), field-programmable gate arrays (FPGA), etc.

Vision sensors $108_{1-N}$ may take various forms, including two-dimensional (2D) cameras and/or other forms that are capable of detecting depth or range ("depth" and "range" will be used herein interchangeably). In the latter case, a vision sensor 108 may be a stereoscope camera, and/or may include multiple 2D cameras that are operated in cooperation as a stereoscopic vision sensor. In some implementations, a single camera may be operated as a de facto stereoscopic camera by capturing two images in succession from slightly different angles (e.g., as the vehicle 107 carrying the camera moves) and processing them using stereoscopic techniques. Additionally or alternatively, in some implementations, one or more vision sensors 108 may take the form of a range-capable sensor such as a light detection and ranging (LIDAR) sensor.

Techniques described herein may be performed in whole or in part by various components depicted in FIG. 1. For example, aspect(s) of agricultural information system 104 may be implemented in whole or in part on client device(s) 106, agricultural information system 104, and/or by the computing node(s) mentioned previously.

Each client device 106, may operate a variety of different applications that may be used, for instance, to obtain and/or analyze various agricultural inferences that were generated using techniques described herein. For example, a first client device $106_1$ operates agricultural (AG) client 107 (e.g., which may be standalone or part of another application, such as part of a web browser). Another client device 106x may take the form of a HMD that is configured to render 2D and/or 3D data to a wearer as part of a VR immersive computing experience. For example, the wearer of client device 106x may be presented with 3D point clouds representing various SOC measurement predictions for points along a terrain map of a field 112. The wearer may interact with the presented data, e.g., using HMD input techniques such as gaze directions, blinks, etc. Other client devices 106 may operate similar applications.

Individual farm vehicles 107 may take various forms. As shown in FIG. 1 and mentioned previously, some farm vehicles may be operated at least partially autonomously, and may include, for instance, unmanned aerial vehicle $107_1$ that carries a vision sensor $108_1$ that acquires vision sensor data such as digital images from overhead field(s) 112. Other autonomous farm vehicles (e.g., robots) not depicted in FIG. 1 may include a robot that is propelled along a wire, track, rail or other similar component that passes over and/or between crops, a wheeled robot, or any other form of robot capable of being propelled or propelling itself past/through/over field(s) 112 of interest. In some implementations, different autonomous farm vehicles may have different roles, e.g., depending on their capabilities. For example, in some implementations, one or more robots may be designed to acquire data, other robots may be designed to manipulate plants or perform physical agricultural tasks, and/or other robots may do both. Other farm vehicles, such as a tractor $107_2$, may be autonomous, semi-autonomous, and/or human-driven. As noted above, any of farm vehicles 107 may be equipped with various types of sensors, such as vision sensors $108_{1-N}$. Farm vehicles 107 may be equipped with other sensors as well, such as inertial measurement unit (IMU) sensors, Global Positioning System (GPS) sensors, X-ray sensors, moisture sensors, barometers (for local weather information), photodiodes (e.g., for sunlight), thermometers, etc.

In various implementations, agricultural information system 104 may be implemented across one or more computing systems that may be referred to as the "cloud." Agricultural information system 104 may include various components that, alone or in combination, perform selected aspects of the present disclosure. For example, in FIG. 1, agricultural information system 104 includes a local data module 116, an operational inference module 120, an SOC inference module 128, and a UI module 130. Agricultural information system 104 may also include one or more databases 115, 121 for storing various data used by and/or generated by modules 116-128, such as data gathered by sensors carried by farm vehicles 107, agricultural inferences, machine learning models that are applied and/or trained using techniques described herein to generate agricultural inferences, and so forth. In some implementations one or more of modules 116-128 may be omitted, combined, and/or implemented in a component that is separate from agricultural information system 104.

Local data module 116 may be configured to gather, collect, request, obtain, and/or retrieve ground truth observational data from a variety of different sources, such as agricultural personnel and sensors and software implemented on robot(s), aerial drones, and so forth. Local data module 116 may store that ground truth observational data in one or more of the databases 115, 121, or in another database (not depicted). This ground truth observational data may be associated with individual agricultural fields or particular positional coordinates within such field(s), and may include various types of information derived from user input and sensor output related to soil composition (e.g., soil aeration, moisture, organic carbon content, etc.), agricultural management practices (e.g., crop plantings, crop identification, crop rotation, irrigation, tillage practices, etc.), terrain (e.g., land elevation, slope, erosion, etc.), climate or weather (e.g., precipitation levels/frequency, temperatures, sunlight exposure, wind, humidity, etc.), and any other features, occurrences, or practices that could affect the agricultural conditions of the field(s) and which could be identified based on analyzing sensor output and/or user input and/or generated based on such identified data.

Local data module 116 may process the ground truth observational data and store the processed observational data in one or more of the databases 115, 121, or in another database (not depicted). Processed observational data may be normalized and/or missing values may be imputed. For example, climate features may be sampled at a higher frequency than, for instance, terrain features, and therefore, local data module 116 may impute missing terrain features in order that dimensions of climate features and terrain features correspond to each other. In some implementations, local data module 116 may use one or more machine learning models stored in one or more of the databases to process the observational data. For example, a machine learning model employed by local data module 116 may correlate information included in the observational data into clusters (e.g., using supervised clustering techniques or unsupervised clustering techniques such as K-means) based on temporal and/or categorical relationships between the data points of the clusters. Thus, such a machine learning model may cluster together soil organic carbon content measurements and crops known to have been grown during certain growing seasons. Such a machine learning model may also cluster together various operational data points that affect water intake/outtake of plants, e.g., soil moisture measurements, ambient humidity levels, precipitation levels/frequency, irrigation levels/frequency, etc.

Local data module 116 may leverage the same machine learning model or another machine learning model and/or observational data clusters to generate the normalized and/or imputed data or to determine which categories of observational data need such normalizations or imputations performed. Thus, for example, the machine learning model may impute land slope values for several points within a growing season based on the observational data indicating high levels and frequency of precipitation (which may indicate several potential instances of erosion). Likewise, the machine learning model may determine that land slope values taken at the beginning and end of the growing season have stayed the same, and precipitation levels and frequency were low (indicating few potential instances for erosion), so two land slope values for the growing season is sufficient and imputing more such values is not necessary.

Operational inference module 120 may be configured to process digital images acquired by vision sensors $108_{1-N}$, and in some implementations, process observational data provided by local data module 116, to infer operational agricultural management practices employed in the field(s) 112. Operational inference module 120 may employ various techniques to infer operational agricultural practices employed in the field(s). In some implementations, operational inference module 120 may infer operational agricultural management practices using one or more machine learning models stored in database 115. A machine learning model that is used in such a context may take various forms, including but not limited to a convolutional neural network (CNN).

In some implementations, a machine learning model employed by operational inference module 120 may be trained to perform object recognition, in which case its output may be indicative of bounding shapes such as bounding boxes. Additionally or alternatively, in some implementations, such a machine learning model may be trained to perform image segmentation, in which case its output may be pixel-wise annotations (or pixel-region-annotations).

Other, segmentation and/or object recognition techniques that may or may not be implemented using artificial intelligence, such as thresholding, clustering, compression-based methods, histogram-based methods, region-growing methods, partial differential equation-based methods, graph partitioning methods, watershed methods, and so forth, are also contemplated.

In some implementations in which multiple vision sensors 108 contribute digital images taken from different heights (e.g., using land-based robots and aerial drones), one or more portions of the digital images may capture the same object(s) at different levels of image resolution or granularity at the same time, relatively the same time (e.g., within the hour or day.), or at different times (e.g., during different growing seasons). Accordingly, operational inference module 120 may be configured to normalize the operational data resulting from processing the digital images and/or to impute missing values of the operational data.

For example, land-based robots may capture digital images of plant, soil, and terrain features of a portion of an agricultural field at a relatively closer distance and higher frequency than an aerial drone captures digital images of plant, soil, and terrain features of the entire agricultural field. Operational inference module 120 can thus normalize the operational data and/or impute missing operational data for the portions of the agricultural field outside of the land-based robot's field of view in order that the dimensions of the operational data for the portion of the agricultural field and the entire agricultural field correspond to one another. In such an example, a vision sensor 108 of a land-based vehicle (e.g., tractor $107_2$, a robot, etc.) may capture portions of the field before and during/after the field is tilled, while a higher elevation vision sensor 108, such as the vision sensor $108_1$ of the aerial drone $107_1$, may do likewise. While the granularity of the digital images captured via the land-based vehicle may be sufficient to infer tillage practices used or changes in soil aeration, the digital images captured by aerial drone $107_1$ may have been captured at too great of a height to detect such operational data points. However, operational inference module 120 may infer that portions of the field not captured via the land-based vehicle experienced the same inferred tillage practices and/or change in soil aeration based on correlating locations, colors, and textures captured in each time-correlated set of images (e.g., based on detecting that the whole field was several shades darker after the digital images from the robot indicated the soil had been tilled).

Based on this data, operational inference module 120 may be configured to make a variety of different agricultural practice management inferences. For example, operational inference module 120 may apply, as input, temporally correlated processed operational data that includes normalized and/or imputed plant, soil, and terrain data across one or more time-series machine learning models stored in database 115 or 121 to generate output indicative of predicted agricultural management practices. In some implementations, operational inference module 120 may additionally use some or all of the observational data points obtained and/or generated by local data module 116 (e.g., that correspond temporally or that are preprocessed to correspond temporally with operational data) to infer agricultural management practices.

Agricultural management practices that operational inference module 120 may infer based on operational data (and, in some implementations, further based on observational data such as digital images captured by robots) include which crops are planted at certain times, which crops are harvested at certain times, irrigation practices, tillage practices, fertilizer treatments, crop rotations, and any other agricultural management practices that cause visible changes to conditions in the agricultural fields and that can affect soil organic carbon content of the field(s). For example, based on processing sequences of digital images and user inputs indicating fertilizer treatments, operational inference module 120 can infer when and where the same or similar fertilizer treatments were applied to the agricultural field(s) even for times that do not have corresponding user inputs indicating such treatments (e.g., based on correlating the fertilizer treatments indicated by the user inputs with soil color changes, soil moisture changes, resulting plant growth spurts, and point in the growing season indicated by the digital images and/or by one or more additional user inputs).

SOC inference module 128 can receive, gather, or otherwise obtain the digital images, the operational data, and observational data in order to use the types of data to generate predicted SOC measurements for the field(s) 112. In some implementations, SOC inference module 128 may process the operational data, observational data, and inferences generated based on such data in order to temporally correlate such forms of data. For example, the processed operational data, processed observational data, and inferences generated based on such data may be grouped into temporal chunks, with each chunk corresponding temporally with at least one of the digital images. SOC inference module 128 may then iteratively apply the digital images 260, along with the temporal chunks of data, to one or more time-series machine learning models stored in database 115 or 121 to generate one or more outputs indicative of SOC content or changes in SOC content for the field(s).

In some implementations, the output(s) may include predicted SOC measurements for the field(s) 112. The predicted SOC measurements for the field(s) 112 may include predicted SOC measurements for particular locations in the field(s) 112, e.g., at various times during a particular time period.

In some implementations, the outputs generated by operational inference module 120 may include inferences about various agricultural conditions predicted to affect SOC content of the field(s) 112, which SOC inference module 128 may use to generate the predicted SOC measurement(s) for the field(s) 112. For example, the inferences about agricultural conditions predicted to affect SOC content may include inferences generated based on time-dependent models that indicate soil aeration, soil moisture, drainage conditions of the soil, crop growth or crop growth rates, implemented crop and/or cover crop rotations, crop yields, terrain slope, terrain erosion or terrain erosion rates, ambient humidity levels, etc., observed in the field(s) over a particular time period. In some such implementations, the outputs generated by operational inference module 120 may further include inferences about various agricultural management practices that correspond to these various agricultural conditions that are predicted to affect SOC content of the field(s) 112. For example, the inferences about agricultural practices may include inferences indicative of the changes in soil aeration, soil moisture, drainage conditions of the soil, crop growth or crop growth rates, implemented crop and/or cover crop rotations, crop yields, terrain slope, terrain erosion or terrain erosion rates, ambient humidity levels, etc. that correspond to the changes in the agricultural conditions that affect SOC content caused by given agricultural management practices implemented in the field(s) during the particular time period.

SOC inference module 128 may process these time-dependent inferences indicating the agricultural conditions and/or changes in agricultural conditions over time, determine their cumulative effect on SOC content for various points in time over the time period, and predict SOC measurements for particular locations in the field(s) 112 at various times during the particular time period. In some implementations, SOC inference module 128 may generate the SOC measurement predictions using the same machine learning model used to generate the inferences about agricultural conditions/practices or another machine learning model.

In some implementations, one or more of the machine learning model(s) used by the SOC inference module 128 may be the same machine learning model(s) used by the operational inference module 120 and/or the local data module 116. In such implementations, the outputs of the layers of the machine learning model(s) used by the operational inference module 120 and/or the local data module 116 may be applied, as input, to other layer(s) of the machine learning model(s) used by the SOC inference module 128. The machine learning model(s) employed by SOC inference module 128 may be trained based on a difference or "error" between the output and ground truth measurements of SOC content. In some implementations, this may include employing techniques such as gradient descent and/or back propagation to adjust various parameters and/or weights of a neural network. In various implementations, one or more of the machine learning models employed by local data module 116, operational inference module 120, and/or SOC inference module 128 may take the form of recurrent neural network(s) ("RNN"), the aforementioned CNNs, long short-term memory ("LSTM") neural network(s), gated recurrent unit ("GRU") recurrent network(s), feed forward neural network(s), or other types of memory networks.

In some implementations, one or more of the machine learning models employed by SOC inference module 128, may be trained as described above using digital images, processed operational data, and processed operational data. Once trained, one or more of the machine learning models may be applied by SOC inference to generate the predicted SOC measurements for the field(s) 112 as output(s) for subsequent time periods using subsequently captured/received digital images (e.g., without requiring the ground truth observational data or any pre-processed operational or observational data). One such implementation of a trained machine learning model is described in more detail with respect to FIG. 4.

In some implementations, to further reduce computational complexity (and in turn, latency, required computing resources, etc.), the digital images may first be processed, e.g., using a machine learning model such as a CNN, to generate reduced-dimensionality embedding(s) (e.g., in latent space). These embeddings may then be applied as input across one or more other machine learning models trained to infer agricultural practices/conditions and/or to generate predicted SOC measurements.

SOC inference module 128 may provide the predicted SOC measurements to AG client 107. AG client 107 may in turn generate output that conveys the predicted SOC measurements in some fashion. For example, AG client 107 may report the predicted SOC measurements directly (e.g., chart(s) showing SOC measurement predictions, map(s) showing location(s) of predicted SOC measurements, etc.).

UI module 130 may provide an interface through which applications such as AG client 107 may interface with agricultural information system 104 in order to implement selected aspects of the present disclosure. As one non-limiting example, UI module 130 may generate and/or distribute scripts, executable files, and/or interactive documents written in markup languages such as hypertext markup language (HTML) and/or extensible markup language (XML) (e.g., "web pages"). A user associated with an agricultural entity may operate an application on a client device 106 such as a web browser (not depicted) or AG client 107 to interact with these items. Additionally or alternatively, in some implementations, UI module 130 may provide an application programming interface (API) to which AG client 107 may connect. In some such implementations, AG client 107 may render its own GUI based on data exchanged with UI module 130.

UI module 130 may be configured to render, or cause a client device 106 to render, as part of a GUI, predictions of SOC content and/or predictions of changes in SOC content. In some implementations, the GUI can further include indications of one or more factors that SOC inference module 128, or the machine learning model(s) employed by SOC inference module 128, have identified as having influenced the predictions. For example, the GUI can include indications of certain agricultural management practices, such as particular crop rotations, or certain agricultural conditions, such as erosion rates, that were weighted heavily in determining the predictions.

Figure 2:
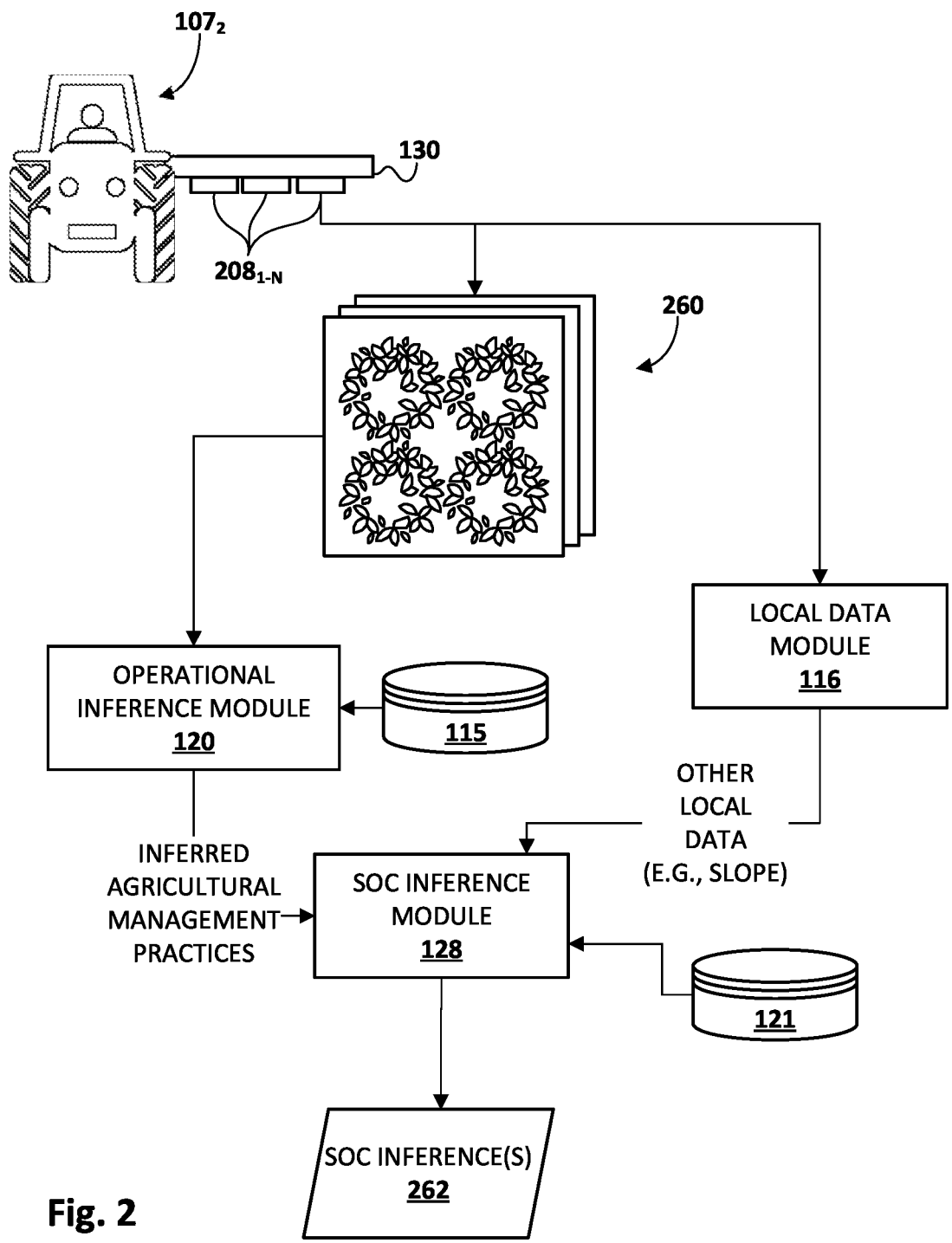
FIG. 2 schematically depicts an example of how data may flow between and be processed by various components described herein.

FIG. 2 depicts an example process pipeline for generating soil organic carbon content predictions in accordance with various implementations described herein. Various components depicted in FIG. 2 may be implemented using any combination of software and hardware, and in some cases may be implemented as part of agricultural information system 104. Moreover, the configuration of FIG. 2 is for illustrative purposes and is not meant to be limiting. Boom 130 mounted to tractor $107_2$ is being carried over a row of plants. Boom 130 may include, for instance (and not depicted in FIG. 2), sprinklers for irrigation, sprayers for chemical application, etc. Also mounted on boom 130 are a plurality of modular computing nodes $208_{1-N}$ that are configured with selected aspects of the present disclosure. Although shown as boxes on the bottom of boom 130 in FIG. 2, modular computing nodes $208_{1-N}$ may alternatively be mounted at other locations of boom 130, such as on its sides or top. And while three modular computing nodes $208_{1-N}$ are depicted in FIG. 2, any number of modular computing nodes 208, such as a single modular computing node $208_1$, may be deployed in similar fashions.

One or more of the modular computing nodes $208_{1-N}$ may include one or more vision sensor(s) $108_{1-N}$ and one or more processing modules, such as at least one of local data module 116, operational inference module 120, or SOC inference module 128, and may perform some or all of the processes performed by agricultural information system 104. In some implementations, one or more of the modular computing nodes $208_{1-N}$ of FIG. 2 may communicate with one another or with one or more portions of agricultural information system 104 to perform aspects of the present disclosure.

Starting at top, one or more ground truth digital images 260 depicting plants, soil, and/or terrain may be captured and/or retrieved from a database, such as database 115. These ground truth digital images 260 may be captured, for instance, by one or more of the vision sensors $108_{1-N}$ configured to capture vision data that are attached to the boom 130 of tractor $107_2$ as tractor $107_2$ moves between the rows of plants in an agricultural field 112.

Local data module 116 may be configured to gather, obtain, or receive observational data from one or more sensors other than vision sensors $108_{1-N}$ (e.g., moisture sensors, location sensors, accelerometers, gyroscopes, sensors configured to measure soil makeup, etc.) and from user inputs (e.g., agricultural personnel inputs to AG client 107). Local data module 116 may process the sensor output and/or user inputs to generate ground truth observational data as well as normalized or imputed observational data, as discussed above with respect to FIG. 1. The observational data may be stored in database 115 or 121, or in another database (not depicted), and used subsequently by the SOC inference module 128 to generate SOC inferences 262.

Meanwhile, operational inference module 120 may be configured to process digital image(s) 260 and/or operational data to infer agricultural management practices—particularly tillage, cover crops, and/or crop rotation practices—used in the field(s), as discussed above with respect to FIG. 1. The inferred agricultural management practices may be stored in database 115 or 121, or in another database (not depicted), and used subsequently by the SOC inference module 128 to generate SOC inferences 262.

SOC inference module 128 may process the observational data, and the inferred agricultural management practices (and the digital images in some implementations) in order to form SOC inferences 262. In some implementations, SOC inferences 262 can include predicted SOC measurements for the field(s). These predictions of SOC measurements for the field(s) may include predicted SOC measurements for particular locations in the field(s) at In some implementations, agricultural workers may be able to provide hypothetical observational and/or operational data for future time periods to local data module 116 for SOC inference module 128 to make SOC inferences 262. Thus, for example, an agricultural worker may input a new tillage practice expected to be implemented in the next growing season. In such an example, SOC inference module 128 can adjust or impute several points of observational data likely to be affected by the new tillage practice (e.g., soil aeration) based on historical observational and operational data in order to predict an overall change in SOC content that the new tillage practice is likely to cause.

Figure 3:
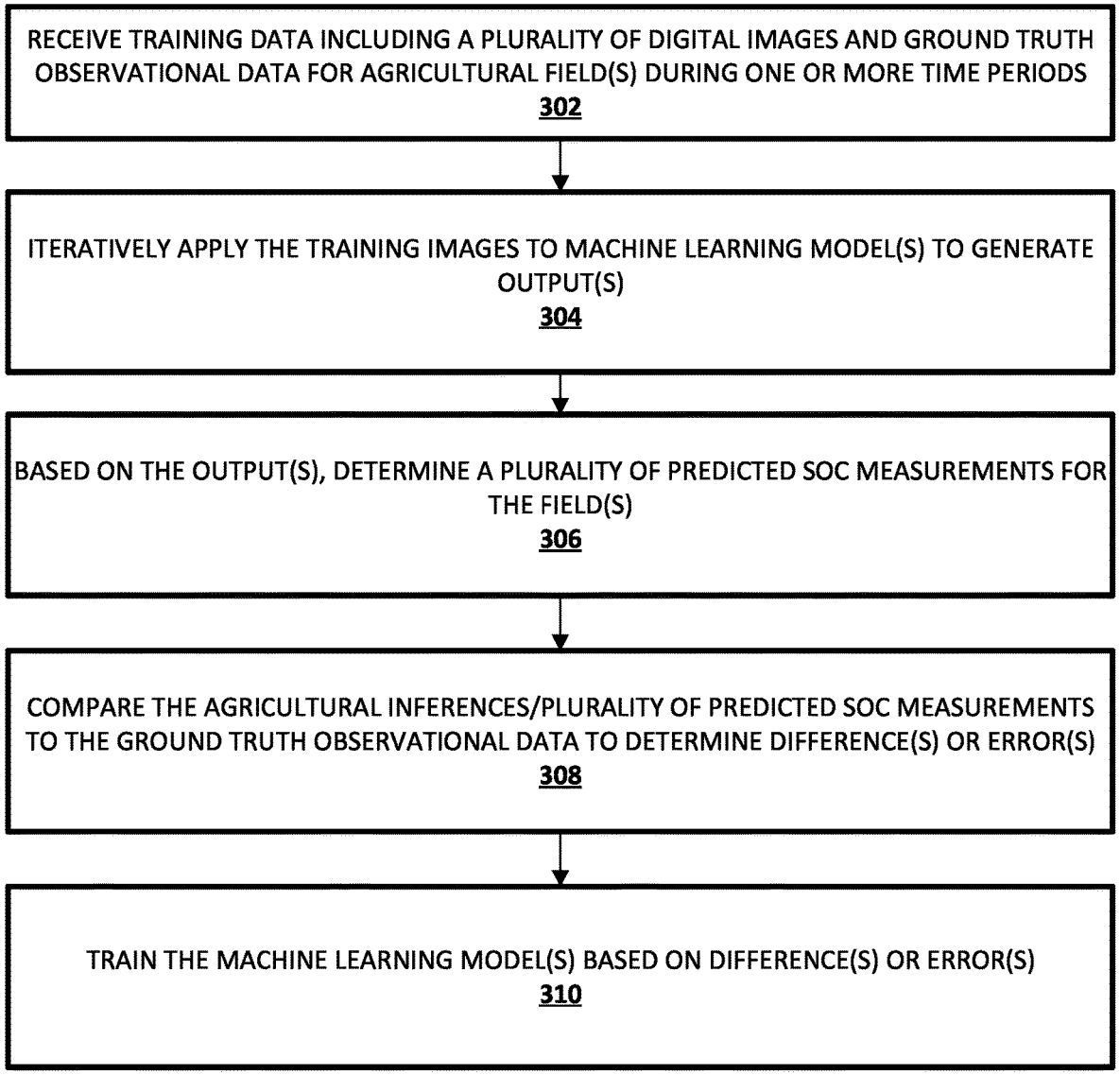
FIG. 3 schematically depicts an example method for practicing selected aspects of the present disclosure, in accordance with various implementations.

FIG. 3 is a flowchart illustrating an example method 300 for training a machine learning model to generate output that is indicative of predicted SOC content, in accordance with implementations disclosed herein. For convenience, the operations of the flowchart are described with reference to a system that performs the operations. This system may include various components of various computer systems, such as one or more components of the client device(s) 106$_{1-N}$, the agricultural information system 104, and/or the AG client(s) 107. Moreover, while operations of method 300 are shown in a particular order, this is not meant to be limiting. One or more operations may be reordered, omitted, or added.

At block 302, the system may receive training data including a plurality of digital images capturing various portions of one or more agricultural fields and a plurality of ground truth observational data (e.g., climate, data points that collectively form a slope map) for the one or more agricultural fields for one or more time periods. In various implementations, the ground truth observational data can include ground truth SOC content measurements taken by one or more sensors implemented in the fields, and/or user input provided by agricultural workers that indicates SOC content measurements. The plurality of digital images and the plurality of ground truth observational data may be obtained from one or more databases including such historical data about the fields, such as database 115. In some implementations, the training images may be high-resolution digital images obtained, using a multi-camera array installed on a combine, tractor, or other farm machinery, at a plurality of positions along a length of a row (e.g., in a field) of a field (e.g., as the combine, tractor, or other farm machinery moves along the length of the row in the field for which SOC content is to be predicted).

At block 304, the system may iteratively apply digital images of the plurality of digital images as inputs across a time-series machine learning model to generate one or more outputs.

Based on the one or more outputs generated at block 304, at block 306, the system may determine a plurality of predicted measures of SOC. At block 308, the system may compare the plurality of predicted measures of SOC to the corresponding ground truth measures of SOC, e.g., to determine differences and/or errors. At block 310, the system may train the time-series machine learning model based on the comparing and/or the differences/errors determined therefrom, e.g., using techniques such as gradient descent, back propagation, etc.

Figure 4:
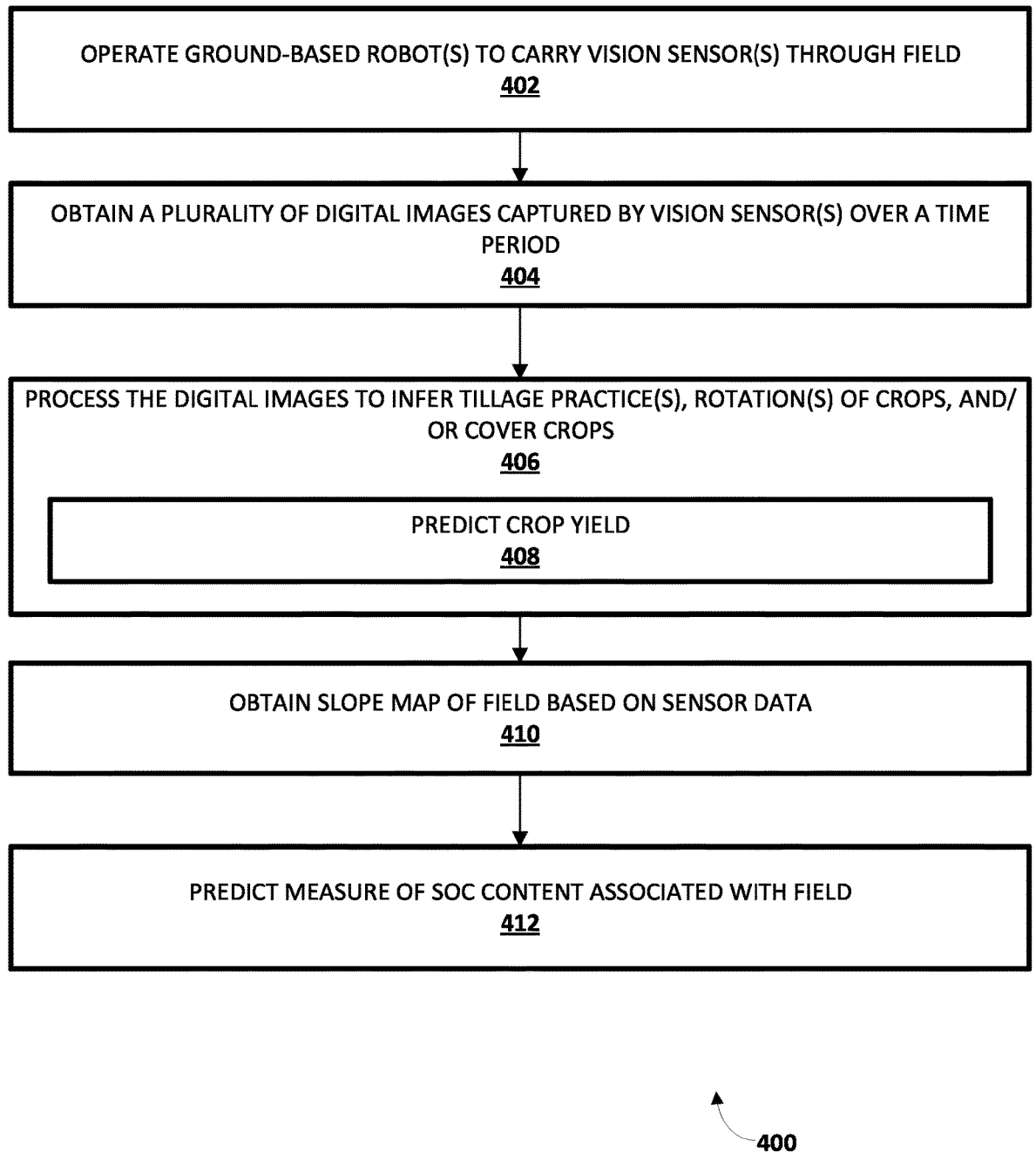
FIG. 4 schematically depicts another example method for practicing selected aspects of the present disclosure, in accordance with various implementations.

FIG. 4 is a flowchart illustrating an example method 400 for using a trained machine learning model to infer/predict SOC measurements, in accordance with the disclosure herein. For convenience, the operations of the flowchart are described with reference to a system that performs the operations. This system may include various components of various computer systems, such as one or more components of the client device(s) 106$_{1-N}$, the agricultural information system 104, and/or the AG client(s) 107. Moreover, while operations of method 400 are shown in a particular order, this is not meant to be limiting. One or more operations may be reordered, omitted, or added.

At block 402, the system may operate one or more ground-based vehicles such as robots or tractors to carry one or more vision sensors through an agricultural field. At block 404, the system may obtain a plurality of digital images captured by the one or more vision sensors over a time period. These digital images may be captured from various perspectives, such as to the sides of crops, overhead, etc.

At block 406, the system may process the plurality of digital images to infer various pieces of information, such as one or more tillage practices implemented in the field over the time period, a rotation of crops planted in the field over the time period, and/or cover crops planted in the field. In some implementations, at block 408, crop yield may be predicted as well (crop yield may be correlated with SOC extracted from and/or added to the soil). At block 410, the system may obtain a slope map of the field based on sensor data generated by sensors carried by the same land-based vehicles, or from other data sources.

Based on the various information inferred at blocks 406-408, and on the slope map obtained at block 410, at block 412, the system may predict a measure of SOC associated with the field. For example, the various data obtained and/or inferred in previous blocks may be preprocessed as applicable and then applied as input across a machine learning model to generate output. The output may be indicative of the predicted measure(s) of SOC content.

Figure 5:
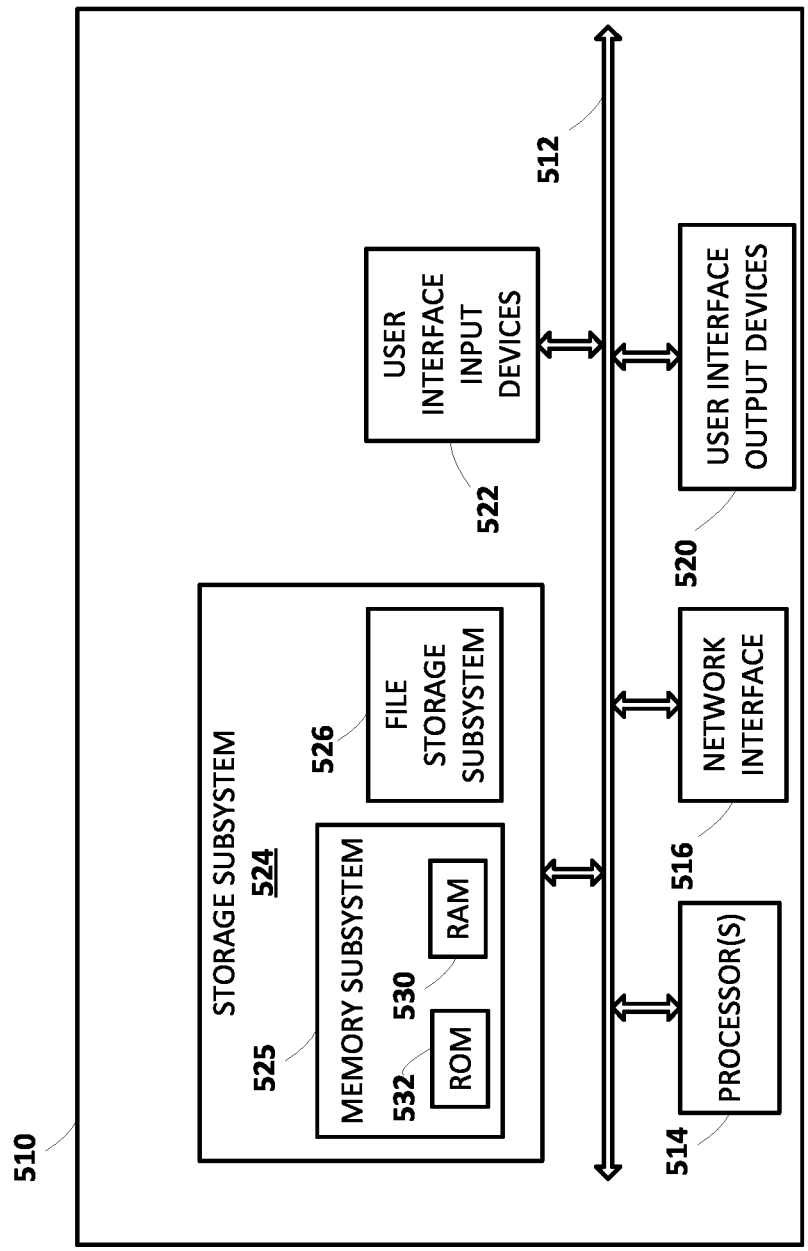
FIG. 5 schematically an example computer architecture that may implement selected aspects of the present disclosure.

FIG. 5 is a block diagram of an example computing device 510 that may optionally be utilized to perform one or more aspects of techniques described herein. Computing device 510 typically includes at least one processor 514 which communicates with a number of peripheral devices via bus subsystem 512. These peripheral devices may include a storage subsystem 524, including, for example, a memory subsystem 525 and a file storage subsystem 526, user interface output devices 520, user interface input devices 522, and a network interface subsystem 516. The input and output devices allow user interaction with computing device 510. Network interface subsystem 516 provides an interface to outside networks and is coupled to corresponding interface devices in other computing devices.

User interface input devices 522 may include a keyboard, pointing devices such as a mouse, trackball, touchpad, or graphics tablet, a scanner, a touchscreen incorporated into the display, audio input devices such as voice recognition systems, microphones, and/or other types of input devices. In some implementations in which computing device 510 takes the form of a HMD or smart glasses, a pose of a user's eyes may be tracked for use, e.g., alone or in combination with other stimuli (e.g., blinking, pressing a button, etc.), as user input. In general, use of the term "input device" is intended to include all possible types of devices and ways to input information into computing device 510 or onto a communication network.

User interface output devices 520 may include a display subsystem, a printer, a fax machine, or non-visual displays such as audio output devices. The display subsystem may include a cathode ray tube (CRT), a flat-panel device such as a liquid crystal display (LCD), a projection device, one or more displays forming part of a HMD, or some other mechanism for creating a visible image. The display subsystem may also provide non-visual display such as via audio output devices. In general, use of the term "output device" is intended to include all possible types of devices and ways to output information from computing device 510 to the user or to another machine or computing device.

Storage subsystem 524 stores programming and data constructs that provide the functionality of some or all of the modules described herein. For example, the storage subsystem 524 may include the logic to perform selected aspects of the methods 300 and 400 described herein, as well as to implement various components depicted in FIGS. 1 and 2.

These software modules are generally executed by processor 514 alone or in combination with other processors. Memory subsystem 525 used in the storage subsystem 524 can include a number of memories including a main random access memory (RAM) 530 for storage of instructions and data during program execution and a read only memory (ROM) 532 in which fixed instructions are stored. A file storage subsystem 526 can provide persistent storage for program and data files, and may include a hard disk drive, a floppy disk drive along with associated removable media, a CD-ROM drive, an optical drive, or removable media cartridges. The modules implementing the functionality of certain implementations may be stored by file storage subsystem 526 in the storage subsystem 524, or in other machines accessible by the processor(s) 514.

Bus subsystem 512 provides a mechanism for letting the various components and subsystems of computing device 510 communicate with each other as intended. Although bus subsystem 512 is shown schematically as a single bus, alternative implementations of the bus subsystem may use multiple busses.

Computing device 510 can be of varying types including a workstation, server, computing cluster, blade server, server farm, or any other data processing system or computing device. Due to the ever-changing nature of computers and networks, the description of computing device 510 depicted in FIG. 5 is intended only as a specific example for purposes of illustrating some implementations. Many other configurations of computing device 510 are possible having more or fewer components than the computing device depicted in FIG. 5.

While several implementations have been described and illustrated herein, a variety of other means and/or structures for performing the function and/or obtaining the results and/or one or more of the advantages described herein may be utilized, and each of such variations and/or modifications is deemed to be within the scope of the implementations described herein. More generally, all parameters, dimensions, materials, and configurations described herein are meant to be exemplary and that the actual parameters, dimensions, materials, and/or configurations will depend upon the specific application or applications for which the teachings is/are used. Those skilled in the art will recognize, or be able to ascertain using no more than routine experimentation, many equivalents to the specific implementations described herein. It is, therefore, to be understood that the foregoing implementations are presented by way of example only and that, within the scope of the appended claims and equivalents thereto, implementations may be practiced otherwise than as specifically described and claimed. Implementations of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present disclosure.

What is claimed is:

1. A method implemented using one or more processors, comprising:
    obtaining a plurality of digital images captured by one or more vision sensors carried throughout a field by one or more ground-based farm vehicles over two or more growing seasons, wherein the plurality of digital images includes at least a first plurality of digital images capturing soil in the field and a second plurality of digital images capturing two or more crops growing in the field over the two or more growing seasons;
    applying at least the first plurality of digital images as input to a first machine learning model trained to generate output indicating one or more tillage practices employed in the field during the two or more growing seasons, wherein the first machine learning model is trained to generate output indicative of tillage practices employed in a given area based on training imagery and ground truth operational data that indicates tillage practices corresponding to the training imagery;
    applying at least the second plurality of digital images as input to one or more additional machine learning models to generate output indicative of the two or more crops grown in the field during the two or more growing seasons, wherein the one or more additional machine learning models are trained to generate output indicative of crops grown in a given area based on input imagery;
    identifying, based on the output indicative of the two or more crops grown in the field during the two or more growing seasons, a rotation of crops implemented in the field over the two or more growing seasons; and
    predicting, based on the one or more tillage practices and the rotation of crops, a measure of soil organic carbon (SOC) associated with the field.

2. The method of claim 1, further comprising obtaining a slope map of the field based on data generated by one or more sensors carried throughout the field by one or more of the ground-based farm vehicles, wherein the predicted measure of SOC is further predicted based on the slope map.

3. The method of claim 1, wherein the processing includes processing the plurality of images to predict a crop yield of the field during a given growing season of the two or more growing seasons, wherein the measure of SOC is further predicted based on the predicted crop yield.

4. The method of claim 3, wherein the crop yield is further predicted based on local climate data or a temporal sequence of high-elevation digital images captured by a satellite.

5. The method of claim 1, further comprising operating a ground-based robot to carry one or more of the vision sensors through the field.

6. The method of claim 1, wherein at least some of the plurality of images are obtained from an edge-computing node that is mounted on a boom of a farm vehicle.

7. The method of claim 1, wherein the plurality of digital images are processed using one or more convolutional machine learning models, and wherein the measure of SOC is predicted using one or more other machine learning models.

8. The method of claim 1, further comprising processing at least a subset of the plurality of digital images using one or more of the additional machine learning models to generate output indicating one or more cover crops planted in the field over the two or more growing seasons, and wherein predicting the measure of SOC associated with the field is performed further based on the output indicating the one or more cover crops planted in the field over the two or more growing seasons.

9. The method of claim 1, further comprising:
receiving indications of one or more tillage practices and rotations of crops likely to be implemented in the field during a future time period; and
predicting a future measure of SOC associated with the field.

10. The method of claim 9, wherein the plurality of digital images further includes high-elevation digital images of the field during the time period captured by one or more satellites or unmanned aerial vehicles ("UAVs").

11. A method implemented using one or more processors, comprising:
obtaining a plurality of digital images captured by one or more vision sensors carried throughout a field by one or more ground-based farm vehicles over a time period wherein the plurality of digital images include at least first digital images capturing soil in the field and at least second digital images capturing a plurality of crops grown in the field;
obtaining ground truth data indicative of a plurality of ground truth measures of soil organic content (SOC) during the time period;
iteratively applying digital images of the plurality of digital images as inputs across a time-series machine learning model to generate outputs indicating time-dependent changes to soil and crop conditions in the field during the time period;
determining one or more agricultural management practices employed in the field during the time period based on the outputs indicating the time-dependent changes to the soil and crop conditions in the field during the time period;
based on the determined one or more agricultural management practices, determining a plurality of predicted measures of SOC;
comparing the plurality of predicted measures of SOC to the corresponding ground truth measures of SOC; and
training the time-series machine learning model based on the comparing.

12. The method of claim 11, wherein the time-series machine learning model comprises a recurrent convolutional neural network.

13. The method of claim 11, wherein the determined agricultural management practices include:
one or more tillage practices implemented in the field over the time period, and at least one of:
crops planted in the field during the time period,
cover crops planted in the field during the time period,
rotations of the crops or the cover crops planted in the field over the time period, or
a slope map of the field during the time period.

14. The method of claim 13, wherein determining the plurality of predicted measures of SOC include processing data indicative of the determined agricultural management practices using the time-series machine learning model or a separate machine learning model.

15. A system, comprising:
a memory device that stores a set of instructions; and
at least one processor that executes the set of instructions to:
obtain a plurality of digital images captured by one or more vision sensors carried throughout a field by one or more ground-based farm vehicles over two or more previous growing seasons, wherein the plurality of digital images includes at least a first plurality of digital images capturing soil in the field and a second plurality of digital images capturing two or more crops growing in the field over the two or more growing seasons;
applying at least the first plurality of digital images as input to a first machine learning model trained to generate output indicating one or more tillage practices implemented in the field during the two or more growing seasons, wherein the first machine learning model is trained to generate output indicative of tillage practices employed in a given area based on training imagery and ground truth operational data that indicates tillage practices corresponding to the training imagery;
applying at least the second plurality of digital images as input to one or more additional machine learning models to generate output indicative of the two or more crops grown in the field during the two or more growing seasons, wherein the one or more additional machine learning models are trained to generate output indicative of crops grown in a given area based on input imagery;
identifying, based on the output indicative of the two or more crops grown in the field during the two or more growing seasons, a crop rotation implemented in the field over the two or more growing seasons;
wherein the tillage practices implemented in the field and the crop rotation implemented in the field over the two or more growing seasons comprises first data;
obtain second data indicative of one or more planned future tillage practices and a planned future rotation of crops in the field over a future growing season;
apply the first data and the second data as inputs to a time-series machine learning model to generate outputs indicating predicted time-dependent changes to soil conditions over the future growing season, wherein the time-series machine learning model is trained based on ground truth operational data indicating agricultural management practices employed in a given area over a given time period and soil sensor measurements taken in the given area before and after the agricultural management practices were employed in the field during the given time period; and determine, based on the outputs indicating the predicted time-dependent changes to soil conditions over the future growing season, a predicted future measure of soil organic content (SOC) for the field.

16. The system of claim 15, wherein the first data includes an inferred crop yield of the field during a particular growing season included in the two or more previous growing seasons.

17. The system of claim 15, further comprising:

obtaining a slope map of the field based on data generated by one or more sensors carried throughout the field by one or more of the ground-based farm vehicles;

wherein data indicative of the slope map is applied as further input to the time-series machine learning model to generate the one or more outputs.

18. The system of claim 15, wherein the plurality of digital images further includes high-elevation digital images of the field during the past time period captured by one or more satellites or unmanned aerial vehicles ("UAVs").

* * * * *